(12) United States Patent
Murphy

(10) Patent No.: US 8,078,254 B2
(45) Date of Patent: Dec. 13, 2011

(54) VIRTUAL TRIAL REDUCTION SYSTEM FOR HIP ARTHROPLASTY AND COORDINATE SYSTEMS THEREFOR

(76) Inventor: Stephen B. Murphy, Winchester, MA (US)

( * ) Notice: Subject to any disclaimer, the term of this patent is extended or adjusted under 35 U.S.C. 154(b) by 886 days.

(21) Appl. No.: 10/565,921

(22) PCT Filed: Jun. 1, 2004

(86) PCT No.: PCT/US2004/017265
§ 371 (c)(1),
(2), (4) Date: Mar. 13, 2006

(87) PCT Pub. No.: WO2005/000140
PCT Pub. Date: Jan. 6, 2005

(65) Prior Publication Data
US 2006/0264731 A1    Nov. 23, 2006

(51) Int. Cl.
*A61B 5/05* (2006.01)
(52) U.S. Cl. ........................... 600/407; 600/587
(58) Field of Classification Search ............ 600/407, 600/587, 424
See application file for complete search history.

(56) References Cited

U.S. PATENT DOCUMENTS

| | | | |
|---|---|---|---|
| 6,096,050 A | 8/2000 | Audette | |
| 6,205,411 B1 * | 3/2001 | DiGioia et al. | 703/11 |
| 6,236,875 B1 | 5/2001 | Bucholz et al. | |
| 6,711,431 B2 | 3/2004 | Sarin et al. | |
| 2002/0035321 A1 | 3/2002 | Bucholz et al. | |
| 2002/0077540 A1 | 6/2002 | Kienzle, III | |
| 2002/0115934 A1 | 8/2002 | Tuke | |
| 2002/0147455 A1 | 10/2002 | Carson | |
| 2003/0130576 A1 * | 7/2003 | Seeley et al. | 600/426 |
| 2004/0254586 A1 * | 12/2004 | Sarin et al. | 606/130 |

FOREIGN PATENT DOCUMENTS

| | | |
|---|---|---|
| EP | 1 628 590 B1 | 4/2009 |
| WO | WO-01/30254 A1 | 5/2001 |
| WO | WO 02/062248 * | 8/2002 |
| WO | WO 02/062248 A1 | 8/2002 |
| WO | WO 02/067784 A2 | 9/2002 |

OTHER PUBLICATIONS

Konishi et al. "Determination of acetabular coverage of the femoral head with use of a single anteroposterior radiograph. A new computerized technique" Journal of Bone and Joint Surgery 1993. 1318-13133.*

Gorton, George et al. "Assessment of the Kinematic Variability Between Twelve Shriners Motion Analysis Laboratories Part 2: Short term follow up" Shriners Hospital for Children, Springfield, MA.

Seidel, Geoffrey K. et al. "Technical Note Hip Joint Center Location From Palpable Bony Landmarks—A Cadaver Study", J. Biomechanics, vol. 28 No. 8 99. 995-998, Elsevier Science Ltd. 1995.

(Continued)

*Primary Examiner* — Max Hindenburg
*Assistant Examiner* — Renee Danega
(74) *Attorney, Agent, or Firm* — Cesari and McKenna, LLP; Martin J. O'Donnell

(57) ABSTRACT

A patient-specific pelvic coordinate system is produced from a single near AP intra-operative image of the patient, obviating the need for use of a patient tracker.

6 Claims, 2 Drawing Sheets

OTHER PUBLICATIONS

David Hebert et al. "Effect of Pelvic Depth and Pelvic Width Measurement on Hip Kinematics and Kinetics", Shriners Hospital for Children, Springfield, MA 01104.
Cheung, Yvonne Y. et al., "A Web-Based Tutorial of Acetabular Fractures Image Analysis", www.bidmc.harvard.edu/radio...arch/CT/cheung_paper/analysis.html, site visited Dec. 10, 2002.
Trousdale, Robert T. et al., "Nonarthroplastic Treatment of Hip Dysplasia in Adults" Hospital Physician, Orthopaedic Surgery Board Review Manual, Orthopaedic Surgery vol. 6, Part 1, Turner White Communications, Inc. 2000.
Marchinda, David et al., "A Comparison Study of Hip Joint Center Location Models," Center for Human Kinetic Studies, Mary Free Bed Hospital and Rehabilation Center, Grand Valley State University, Grand Rapids, MI, http://www.mfbrc.com/MAC/MAChjc%20compare.htm, site visited Dec. 9, 2002.
Terry, Michael A. et al. "Measurement Variance in Limb Length Discrepancy: Clinical and Radiographic Assessment of Interobserver and Intraobserver Variability" Lippincott Williams & Wilkins, J. Pediatr Orthop vol. 25, No. 2, Mar./Apr. 2005.
Vineet K. Sarin, et al., "Accurate Femur Repositioning is Critical During Intraoperative Total Hip Arthroplasty Length and Offset Assessment" Kinamed Navigation Systems LLC, Camarillo, California and Alta Orthopaedics, Santa Barbara, CA, Elsevier Inc. 2005.
Cuckler, John M., "Limb Length and Stability in Total Hip Replacement," Hip Arthroplasty: Avoiding Pitfalls, Managing Problems, Sep. 2005.
Kiefer, Hartmuth et al. OrthoPilot Total Hip Arthroplasty Workflow and Surgery, Orthopedics, Oct. 2005, vol. 28, No. 10/Supplement, Department of Orthopaedic and Trauma Surgery at Lukas Hospital.
Goldstein, Wayne M. et al. "Leg Length Inequality in Total Hip Arthroplasty" Orthopedics, Sep. 2005, vol. 28, No. 9/Supplement.
Konyves, A. et al. "The Importance of Leg Length Discrepancy After Total Hip Arthroplasty," The Journal of Bone and Joint Surgery, vol. 87-B, No. 2, Feb. 2005.
Lazovic, Djorgje et al. "Results with Navigated Bicontact Total Hip Arthroplasty" Orthopedics, Oct. 2005, vol. 28, No. 10/Supplement.
Sarin, Vineet K. et al. "Accurate Femur Repositioning is Critical During Intraoperative Total Hip Arthroplasty Length and Offset Assessment," The Journal of Arthroplasty, vol. 20, No. 7, 2005.
Moers, R. European Patent Office Communication for Application No. 04776221.6-1265, Jun. 29, 2006.
Acetabular Fractures, http://www.amirmd.com/ortho-info/acetabularfx.html, site visited Feb. 16, 2006.
Murphy, Stephen B. Murphy et al., "Acetabular Dysplasia in the Adolescent and Young Adult," Department of Orthopaedic Surgery, Children's Hospital Medical Center and Massachusetts General Hospital, Boston, MA, Presented at 18th Open Scientific Meeting of the Hip Society, Feb. 11, 1990.
Starr, Roland et al., "A New Model of Three Dimensional Trunk Kinematics" Hugh Williams Gait Laboratory, Royal Children's Hospital, Parkvill, VIC, Australia.
Bell, Alexander L. et al. "A Comparison of the Accuracy of Several Hip Center Location Prediction Methods" J. Biomechanics vol. 23, No. 6 pp. 617-621, 1990.
D'Lima, Darryl D. et al., "Standard for Hip Joint Coordinate System Recommendations from the ISB Standardization Committee," pp. 1-8.
"Sulzer Orthopedics Joint Care/ Fracture Care, Converge Porous Acetabular System Surgical Technique" Sulzer Medica, Sulzer Orthopedics Inc. Dec. 2002, Austin, TX.
Ebraheim, Nabil, et al., "Correlation Between Symphesis Pubis' Opening and SIJ's Opening During Open Book Injury" Biomechanics Laboratory, Department of Mechanical, Industrial and Manufacturing Engineering, University of Toledo, Toledo, Ohio.
Kirkwood, R.N. et al. "Radiographic and Non-Invasive Determination of the Hip Joint Center Location: Effect on Hip Joint Angles," Canadian Society for Biomechanics—American Society of Biomechanics, Aug. 14-18, 1998, http://ash-bimech.org/onlineabs/NACOB98/23/, site visited Dec. 9, 2002.
Piazza, Stephen J. et al., "Determinants of the Accuracy of the Functional Method of the Hip Joint Center Location," Center for Locomotion Studies and Departments of Kinesiology.
http://isb.ri.ccf.org/biomch-1/archives/biomch-1-1991-06/00013.html site visited Dec. 9, 2002, Pelvic Orientation.
Lyon, Thomas et al., "Anterior Placement of a Pelvic Stabilizing Clamp: An Anatomical Evaluation of Danger Areas and Comparison of Placement Sites in Normal and Fractured Cadaveric Pelvi" http://www.aaos.org/wordhtml/anmeet99/poster/340.htm, AAOS On-Line Service-1999, site visited Dec. 9, 2002.
Prasad, Srinivas et al., "Minimally-Invasive Approach to Pelvic Osteolysis" Presentation, May 10, 2001.

* cited by examiner

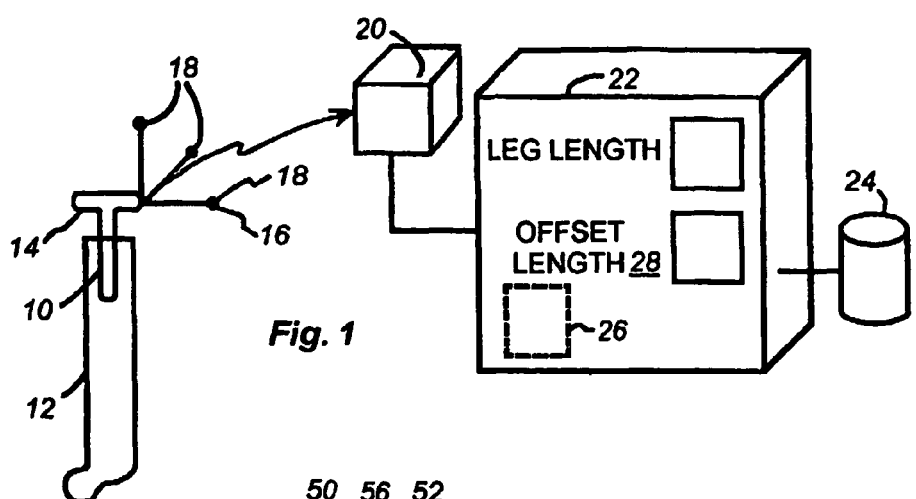
Fig. 1
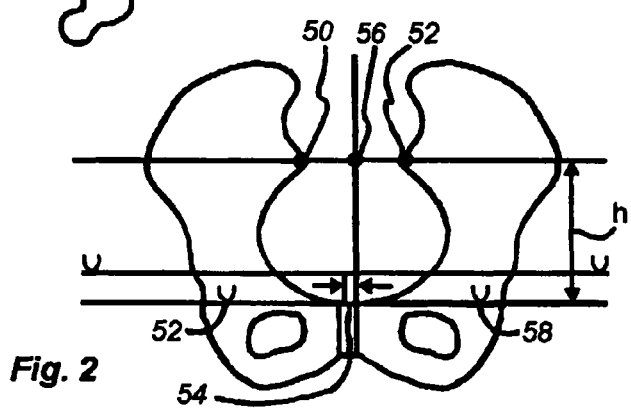
Fig. 2
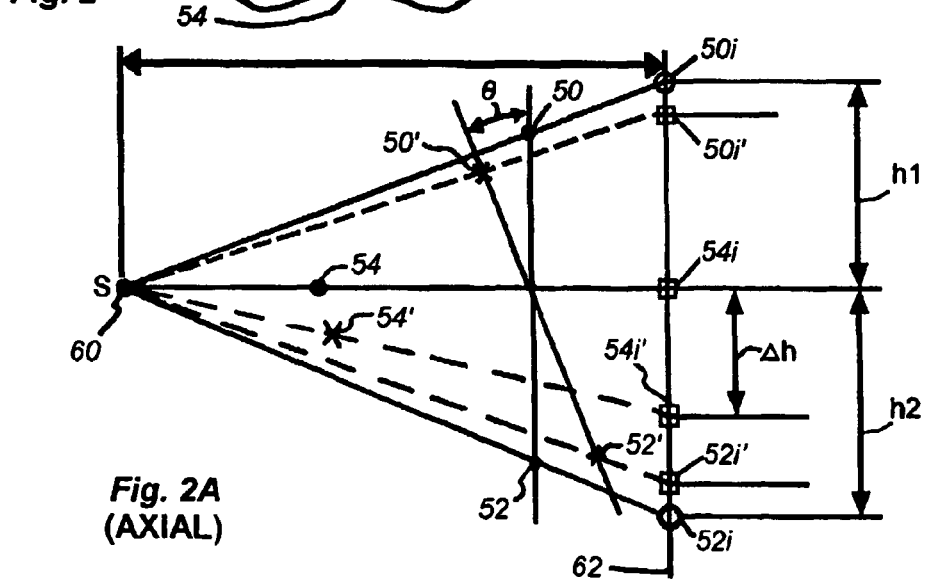
Fig. 2A (AXIAL)

(TRANSAXIAL)

VIRTUAL TRIAL REDUCTION SYSTEM FOR HIP ARTHROPLASTY AND COORDINATE SYSTEMS THEREFOR

BACKGROUND OF THE INVENTION

1. Field of the Invention

The invention relates to apparatus and methods for facilitating total hip arthroplasty.

2. Background Information

Hip arthritis due to malfunctions, fractures and diseases constitute a major source of disability. Reconstruction of the hip, whether involving first time hip replacement or replacement of failed components, is complicated by the great mobility of the hip joint and the uncertainty in the exact position of pelvis and femur during surgery. When a hip joint is replaced, as in total hip arthroplasty, critical factors to assess include changes in leg length, tension of the tissues around the joint, and stability of the replaced hip or its resistance to disassembly, referred to as hip dislocation. These critical factors are generally checked by means of a "trial reduction" (i.e., an insertion of the prosthetic femoral head into the prosthetic acetabulum). It is during this trial reduction that these critical parameters can be assessed to determine if the goals of the reconstruction are being achieved.

This assessment includes moving the femur with respect to the pelvis over ranges of motions, including flexion/extension, adduction/abduction and internal/external rotation. The trial reduction can be used to generally assess leg length, tissue tension, and limits of motion. For example, motion may be limited by tethering of tissues coming under tension, impingement of the prostheses against each other (prosthetic impingement), impingement of the tissues themselves (non-prosthetic impingement), or dislocation of the prosthetic femoral head out of the prosthetic acetabular socket in the absence of, or in advance of, prosthetic impingement.

On detection of unacceptable changes in length, or of an unsafe or restricted range of motion, corrections must be made and the process repeated. This prolongs the operation. Further, failure to optimally place the implants within the body can result in instability of the prosthetic joint or in inappropriate leg length, both of which may require reoperation.

SUMMARY OF THE INVENTION

In accordance with the present invention, I provide an apparatus and method for accurately and efficiently identifying the positions of the pelvis and the femur during surgery; accurately and efficiently placing a trial or real acetabular prosthesis into the pelvis, as well as a trial or real femoral prosthesis into the femur; and then performing a virtual trial reduction of the hip such as in total hip arthroplasty.

The invention makes use of surgical navigation elements that have come into recent use in surgical procedures. Surgical navigation systems use light, sound (specifically, ultrasound) or electromagnetic signals to determine the position of reference elements in an operating room. For example, a reference element placed on a digitizing probe can be tracked by a sensing system in the operating room so as to determine its position very accurately. Knowing the location in three-dimensional space (i.e., the operating room) of the reference elements, and knowing the location of this element with respect to the tip of the probe on which it is mounted, the location of the tip of the probe (and thus anything with which it is in contact) can accurately be determined. Similarly, a reference element may be placed on a body segment such as the pelvis or femur. Critical points on the body segment can then be determined simply by tracking the relative position of the digitizing probe and the body segment. Additionally, line segments can easily be determined by digitizing pairs of points.

The present invention extends prior surgical navigation systems to enable the performance of a "virtual", as opposed to a physical, trial reduction of the hip prior to its actual reduction on completion of the surgical procedure. In particular, in accordance with the present invention, initial measurements of significant parameters of the patient are made and stored. These measurements may include not only the distance between selected landmarks on the patient's pelvis and femur, which enables the surgeon to ensure that desired leg length is maintained or achieved by the operation, but also may include measurements of offset and of the free range of motion, among others, so that these parameters may also be verified after the operation, and the changes resulting from the surgery can be quantified.

In order to make the requisite measurements, suitable coordinate systems must be established for the pelvis and for the femur. Common landmarks for a pelvic coordinate system are the two anterior superior iliac spines and the pubic symphysis. A variety of techniques are currently used to determine (i.e., measure) these landmarks, including direct digitization with a navigated probe (i.e., a probe having reference elements associated with it whose position in three-dimensional space can accurately be determined); by using preoperative three-dimensional CT or MR scan images of the landmarks and thereafter registering the images with the actual landmarks during the operation; or by making multiple fluoroscopic images of the pelvis intraoperatively, digitizing the selected landmarks on the images, and backprojecting them to determine their actual location. All of these methods are inefficient.

Directly digitizing certain landmarks such as the superior spines or the pubic symphysis by touching the skin or probing through the skin requires that these landmarks be accessible during the surgery. Further, the anterior superior iliac spines are ill-defined, rounded landmarks that are difficult to determine accurately by direct digitization. Similarly, developing a pelvic coordinate system by preoperative three-dimensional imaging has a number of shortcomings. To begin with, the patient must undergo a test preoperatively that might otherwise be unnecessary. Further, during surgery, the three-dimensional dataset of the pelvis must be "registered" to the actual pelvis, a procedure which itself can be time consuming. Likewise, developing a pelvic coordinate system by obtaining multiple fluoroscopic images and backprojecting is both time consuming and difficult. Frequently the quality of the images is poor, since they must often be taken at angles that require penetration not only of the patient's body but also of the apparatus that stabilizes the patient and of the operating table as well. Finally, attempting to combine directly digitized information with fluoroscopic images is subject to the drawbacks of both methods.

In order to address these and other problems, in accordance with the present invention, a pelvic coordinate system is created based on a single approximately AP (anterior-posterior) fluoroscopic image of the pelvis taken intra-operatively. The image is preferably formed in a single exposure, but may be formed as a composite of two or more exposures of adjacent or overlapping regions but all from the same orientation, i.e., approximately AP. Hereinafter, this image, whether formed from a single exposure or from a composite of such multiple exposures, will be referred to as a "single" image or, more often, simply as "the" image.

From this image, important landmarks on the pelvis are determined. On the anterior portion of the pelvis, a preferable landmark is the pubic symphysis; the image point on the AP image corresponding to this landmark is referred to herein as "PS". On the posterior portion of the pelvis, preferable landmarks are the inferior portions of the left and right sacroiliac joints; the image points corresponding to these landmarks are referred to herein as "LSIJ" and "RSIJ", respectively. Further useful landmarks are the left and right teardrops ("LTD", "RTD"); as described herein, the teardrops advantageously may be used to provide a first reference axis for a pelvic coordinate system, as well as to provide a reference length for calibrating angular orientation of the pelvis.

Although the size of the pelvis, and thus the distance between designated landmarks on a pelvis, varies from patient to patient, there is considerable consistency of ratios among various landmarks from patient to patient. For example, the ratio of the width of the pelvis (as measured by the interteardrop distance) to the depth of the pelvis is relatively consistent over large groups of patients of the same sex. The same is true of other landmark distances, such as that between the pubic symphysis and posterior landmarks such as the LSIJ and the RSIJ. This consistency is applied to advantage in forming a pelvic coordinate system from the near AP fluoroscopic image.

In particular, on the image, a line extending between the LTD and RTD image points establishes a first reference axis; the distance between these points (the "inter-teardrop" or "ITD" distance) provides a normalization factor for other measurements. A perpendicular from this axis to the midpoint (MPSIJ) between the LSIJ and RSIJ image points provides a second reference axis; for ease of reference, the perpendicular will be referred to as the "MPSIJ-TD" (i.e., "Mid Point of Sacroiliac Joints-to-Tear Drop") axis. In a perfectly-positioned, true AP view of the pelvis, the MPSIJ-TD line would perfectly intersect the pubic symphysis. This would demonstrate that the middle of the anterior portion of the pelvis is directly in front of the middle of the posterior portion of the pelvis, thus confirming that there is no rotation of the pelvis about the longitudinal (or "axial") axis of the body. Conversely, any transverse (transaxial) separation in the near AP image between the image of the midpoint of the pubic symphysis ("MPPS") and the MPSIJ-TD axis indicates axial rotation of the pelvis in relation to the plane of the image. The ratio of this distance to the ITD distance provides a direct indication of the amount of angular rotation.

Transaxial rotation, which is a measure of pelvic flexion/extension, is likewise determined from the near AP fluoroscopic image. Transaxial rotation is determined by measuring the vertical (axial) distance on the image between the sacroiliac midpoint image point (MPSIJ) and the pubic symphysis image point (PS), normalized by dividing by the inter-teardrop (ITD) distance to thereby obtain a numeric index, $k=(MPSIJ-PS)/ITD$. If the pelvis is generally parallel to the fluoroscopic image plane, k will be relatively fixed (i.e., have essentially the same value) over a wide range of same-sex population, say $k_0$. A value of k greater than $k_0$ indicates rotation anteriorly; conversely, a value of k less than $k_0$ indicates rotation posteriorly. The amount of rotation is thus a function of $(k-k_0)$ and accordingly the image point measurements may be corrected for transaxial rotation, as well as for axial rotation, to provide an accurate indication of the position of the pelvis in the operating room coordinate system. Thus, from a single AP image, both axial and transaxial rotation of the pelvis may quickly be determined and corrected for.

Next, a femoral coordinate system is established. This may be done by various known techniques, but is preferably done rapidly and efficiently in further accordance with this invention. First, the trochanteric fossa point, TF, of the femur is digitized directly through the surgical exposure. Next, the medial and lateral epicondyles of the femur are digitized percutaneously. The midpoint of those two points is taken as the center of the knee, CK. The line TF-CK defines the femoral shaft axis, (FSA).

The lower leg axis (LLA) is then digitized with the knee bent 90 degrees. A plane containing the center of the knee, CK, and perpendicular to the Lower Leg Axis (LLA) and another plane containing the center of the knee, CK, and perpendicular to the femoral shaft axis (FSA) intersect in a line defined by the intersection of these two planes; this line is taken as the condylar axis. The condylar plane is then taken as the plane that contains both the femoral shaft axis and the condylar axis.

When the hip joint is sufficiently intact as to have a reasonably well defined center, this center is determined by any of several methods. One known method to determine the hip joint center is to move the unreplaced hip through a range of motion and then calculate the center of rotation of that motion. Another known method is by biplane radiography and backprojection. However, this method requires the taking of multiple fluoroscopic projections, and is thus less desirable.

In accordance with this invention, a preferred method of determining the hip joint center is to first determine the center of rotation on the single near AP image that has been taken for the purpose of determining a pelvic coordinate system. This defines a line upon which the center of hip rotation lies (the adduction/abduction axis). The femur then, instead of being placed through a full range of motion to calculate the center of rotation, may then simply be flexed and extended. The location where the flexion/extension axis, determined kinematically, crosses the adductionl/abduction axis, determined radiographically, is the center of rotation of the hip. The reason that this method is preferred is that when a hip joint becomes arthritic, it usually becomes aspherical to a greater extent in adduction/abduction motion than in flexion/extension motion. This means that the center of rotation, as determined in the adduction/abduction plane is better determined radiographically (since kinematics may be inaccurate) and that the center of rotation, as determined in the flexion/extension plane, is better determined kinematically for the reasons that kinematic flexion/extension determination is likely to be accurate and because images in this plane are difficult to obtain.

When the hip is dislocated, e.g., during surgery, another, known method of determining the center of rotation of the hip is to directly digitize points on the acetabular and femoral head surfaces and calculate the center of each sphere. However, in further accordance with the present invention, this may readily be done by fitting to the femoral head an implement having a spherical recess conforming to the head; a variety of such implements are preferably provided, one for each head size. With a reference frame affixed to the spherical instrument, and knowing the geometry of the implement and of its spherical recess, the center of rotation of the femur can instantly be identified. Similarly an implement in the form of a round ball of known dimension that conforms to the acetabulum may be placed into the acetabulum. Again, knowing the geometry of the implement and with a reference frame affixed to it, the center of rotation of the acetabulum can instantly be determined.

With the femoral head center determined, the femoral coordinate system can be completed. A plane that includes both the femoral shaft axis, FSA, and the center of the femoral head, is then the preoperative anteversion plane. Similarly, during surgery later, a plane that includes the femoral shaft axis, (FSA), and the center of the prosthetic, or trial prosthetic femoral head, is then the new anteversion Plane.

The center of the hip relative to the pelvis and femur is noted so that any changes in the location of these centers that have been effected by the surgery may be calculated. Specifically, superior/inferior and medial/lateral changes in the acetabular center relative to the pelvis and the femoral head center relative to the femur allow exact changes in the leg length and the offset as a result of the reconstruction. This allows comparison of the actual changes with those established as pre-operative goals in order to determine whether those goals have been achieved. Further, the relative contributions of the acetabular and femoral components can be calculated, thereby facilitating any necessary adjustments.

Even when the hip joint does not have a well defined center, the leg length and the offset can still be determined from the known relative positions of the pelvic and femoral coordinate systems, although the separate contributions of the acetabular and femoral components can not be calculated in this case.

In further accordance with the present invention, the position of the acetabular and femoral prosthetic components is determined (i.e., measured) with navigational probes or elements in the course of the operation. Specifically, using a navigation system, the orientation and center position of the original and the replacement acetabulum are determined and stored. With the head and neck removed, a broach is inserted into the femur, using a broach insertion handle. Heretofore, a trial head and a trial neck were then fitted to the broach and a trial reduction (i.e., fitting of the trial femoral head to the replacement acetabulum) was performed and the important parameters (leg length, offset, range of motion, etc.) were determined. Adjustments were made as necessary, and different broaches, broach positions, femoral heads and/or necks were tried with sequential trial reductions until the resultant measurements were acceptable. This could consume considerable time, and lengthened the course of the operation, thus increasing its risks. In particular, since the position of the patient on the operating table is not precisely known, the position of the inserted components is similarly not precisely known, and thus assessments of motion, leg length, and other critical parameters are also imprecise.

In accordance with the present invention, the pertinent dimensions and shapes of the acetabular and femoral components that may be used in a hip replacement are stored in a computer system. A navigation frame is fitted to the broach insertion handle. As the broach is inserted, its position, and thus the position and orientation of any proposed femoral head and neck combination that might be selected for attachment to the broach, together with the resultant change in leg length and offset due to changes on the femoral side, can immediately be determined and provided in real time to the surgeon. Similar computations can be made of changes arising from the acetabular side, and thus the total changes in leg length and offset may be determined accurately without actually performing a reduction. Further, with the hip still disassembled before actual hip joint reduction, the range of motion of the hip with the proposed components may be computed in order to determine whether those components would produce undesirable side effects, such as prosthetic impingement within a desired range of motion. Thus, when the patient is ready for actual reduction of the hip (i.e., insertion of the replacement femoral head into the replacement acetabulum), the determination will already have been made that the selected components and positionings will provide the desired parameters for proper hip operation.

BRIEF DESCRIPTION OF THE DRAWINGS

The invention description below refers to the accompanying drawings, of which:

FIG. 1 shows a navigation coordinate frame attached to a broach handle for providing component position data during a hip replacement operation;

FIGS. 2, 2A and 2B illustrate the determination of the axial and transaxial rotation of the pelvis from a single fluoroscopic image for determination of a pelvic coordinate system for use in the present invention.

DETAILED DESCRIPTION OF AN ILLUSTRATIVE EMBODIMENT

Figure 2B:
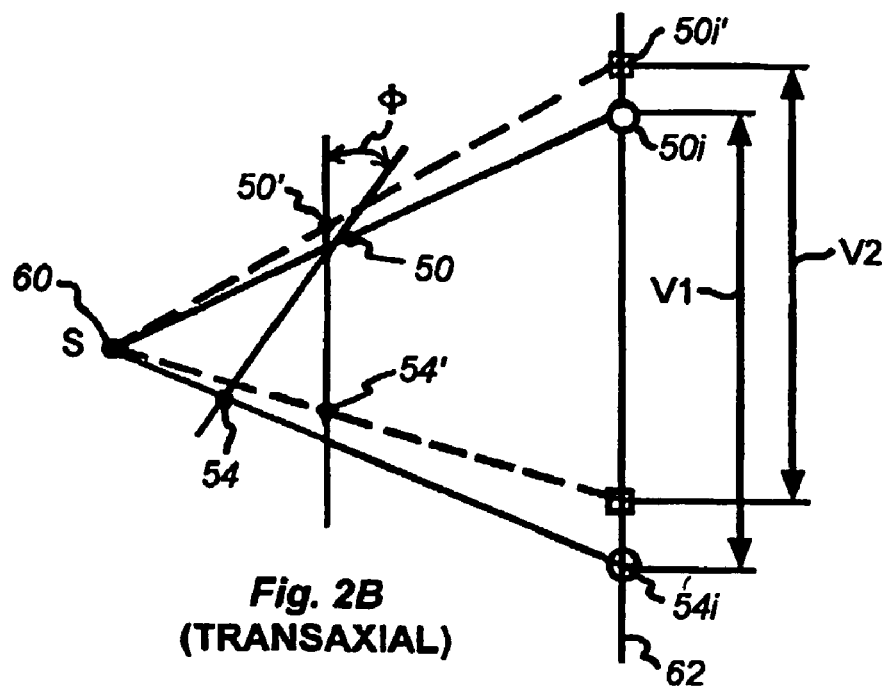
Figure 3:
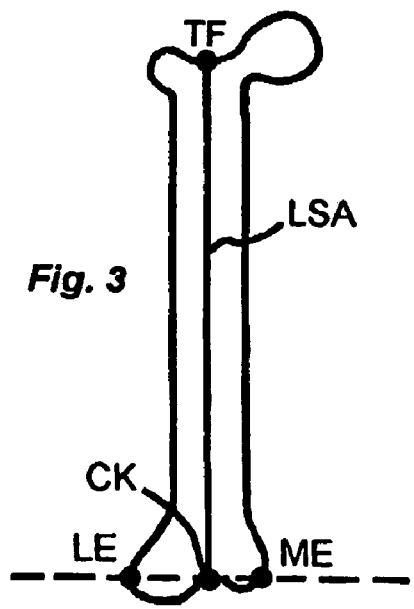
FIG. 3 illustrates the determination of a femoral coordinate system for use in the present invention.

Referring now to FIG. 1, a broach 10 of known geometry that is being inserted within a femur 12 is connected to a broach handle 14 having a navigation frame 16 associated with it. The frame 16 carries a plurality of elements 18 extending in different directions in space. These elements may, for example, be infrared reflective elements such as are commonly used in conventional surgical navigation systems. A controller 20 receives signals from the elements 18 and from these determines the instantaneous position of the broach handle and thus of the broach. The controller may be of conventional type, e.g., an infrared emitter which receives reflections from the elements 18 and from these determines the position (i.e., location and orientation) of the frame with respect to itself and thus with respect to other objects of known relation to it.

The controller 20 in turn provides output to a monitor and controller 22 which provides the functions of an augmented surgical navigation system in accordance with the present invention. In particular, monitor and controller stores data defining the geometry and dimensions of components such as broaches, broach handles, and femoral replacement necks and heads that may be used in total hip arthroplasty. The data is advantageously stored on magnetic disk, such as disk 24, but other forms of data storage may be used if desired.

The monitor and controller 22 advantageously includes a programmed data processor (computer) 26 which uses the data stored on disk 24, as well as navigational data supplied from controller 20 during the course of an operation, to guide the surgeon in performing the operation, as will be described shortly in more detail. To this end, the monitor and controller 22 provides a display area 28 which displays to the surgeon certain information concerning significant parameters pertaining to the procedure being performed, such as leg length, offset, etc.

In order to provide a basis for the measurements to be performed, it is necessary to establish appropriate coordinate systems specific to the patient. In the case of total hip arthroplasty as described herein, these systems comprise a pelvic and a femoral coordinate system. A variety of such systems are known and may be used in the virtual trial reduction system described herein. However, I have found a way of greatly simplifying the determination of these coordinate systems for total hip arthroplasty, and now describe a preferred method for such determination.

Commonly, a multiplicity of X-ray, fluoroscopic or other forms of images are obtained and used in defining a pelvic coordinate system. The procedures typically require images taken from a multiplicity of reference points (front, side, etc.), and are thus time-consuming, and unduly prolong the operation when done during surgery. I have found that sufficient information may be obtained from a near AP (anterior-posterior) fluoroscopic image taken in a single plane as to enable the accurate determination of a pelvic coordinate system. The image may a single image, or may be a composite of two or more laterally offset images formed in the same plane.

Thus, FIG. 2 diagrammatically represents the image of a pelvis as obtained from a near AP fluoroscope projection. In the preferred embodiment of the invention, three pelvic landmarks are used for the coordinate determination, namely, the right and left sacroiliac joints 50 and 52, respectively, and the pubic symphysis 54. The surgeon marks these points with a navigated probe to capture them. If the hip is perfectly aligned with respect to the imaging plane, the pubic symphysis will be found to lie directly below the midpoint of the right and left sacroiliac joints (absence of axial rotation of the pelvis). Further, the distance between the image of the pubic symphysis 54 and the midpoint 56 between the images of the right and left sacroiliac joints 50 and 52, respectively, will represent the true vertical distance between these points, i.e., neither increased nor diminished by transaxial rotation of the pelvis. Under these circumstances, a first pelvic reference axis is established as the line joining the right and left sacroiliac joints 50 and 52, respectively, while a second pelvic reference axis is established as a line connecting the midpoint 56 of these joints and the pubic symphysis 54. A third pelvic reference axis is then established as a line perpendicular to these two.

If, however, the pelvis is tilted with respect to the imaging plane, either in an axial direction (i.e., about a vertical axis through the body, from top to bottom) or transaxially (from side to side), it will be necessary to correct the measurements for this tilt. This is shown in detail in FIGS. 2A and 2B.

FIG. 2A is a view from the top of the body looking down along the axial axis and showing formation of two different fluoroscopic image of the landmarks. In a first image, the pelvis is aligned with the right and left sacroiliac joints 50, 52 (indicated by closed circles), respectively, parallel to the image plane 62 of the fluoroscope. A source 60 of x-rays projects images 50$i$, 52$i$, 54$i$ (indicated by open circles) of the landmarks 50, 52, 54 onto the image plane. Because of the parallel alignment of the sacroiliac joints and the image plane, the image of the pubic symphysis is midway between the images of the sacroiliac joints, i.e., the distances $h_1$ and $h_2$ are equal.

A separate, second, image is also shown in FIG. 2 for comparison. In this image, the pelvis is tilted axially by an angle θ in the axial direction. The landmarks 50, 52, 54 then assume the positions 50', 52', 54' (indicated by x's), respectively. Their images are then shifted to the positions shown as 50$i$', 52$i$', 54$i$' (indicated by rectangles), respectively. The image 54$i$' of the pubic symphysis is no longer midway between the images 50$i$', 52$i$', respectively, of the right and left sacroiliac joint, but is shifted laterally by a distance Δh as shown. The amount of this shift is a measure of the axial rotation. In particular, the rotation is given by sin θ=Δh/L, where L is the distance between the x-ray source 60 and the image plane 62. Thus, by measuring Δh on the fluoroscopic image, the axial rotation θ may be determined and the first pelvic reference axis may then be correctly aligned with the sacroiliac landmarks on the rotated pelvis but based on measurements made in the single fluoroscopic plane.

Because pelvic sizes differ from one person to another, the displacement Δh will be a function of the actual distance between the right and left sacroiliac joints. To correct for variations in this distance from patient to patient, the measured distance is scaled by dividing it by the inter-teardrop distance. The resultant ratio is a direct measure of the axial rotation of the pelvis with respect to the plane of the AP image.

FIG. 2B shows the effect of rotation about the transaxial plane. In this figure, the orientation of a pelvis with zero transaxial rotation is illustrated by sacroiliac joint 50 and pubic symphysis 54 (indicated by filled circles). The images of these landmarks on the imaging plane are shown as images 50$i$, 54$i$, respectively. A second, separate image taken with the hip rotated forwardly (anteriorly) about the transaxial axis by an angle ϕ is shown as having its sacroiliac and pubic symphysis landmarks at rotated positions 50', 54' (designated by x's), respectively. The projections of the latter are shown at 50'$i$ and 54'$i$, respectively, in image plane 62. The change in the vertical height of the distance between the sacroiliac joint and the pubic symphysis, $v_2-v_1$, when divided by the inter-teardrop distance, is a direct measure of the rotation about the transaxial axis.

With the axial and transaxial rotations of the pelvis thus determined, the position of the pelvis in the frame of the operating room, as well as all components attached to it, is accurately known. Similarly, with the femoral coordinate system determined as earlier described, the position of the femur and all components attached to it is accurately known. Thus, as an operation proceeds, the surgeon has instantaneous and accurate information as to the instantaneous location of the affected body parts and prosthetic components and can therefore make a "virtual trial reduction" based on this information prior to performing an actual reduction. This not saves time, but ensures accurate component fit and enhances the likelihood of achieving preoperative goals.

In particular, the surgeon may "try" a variety of prostheses virtually, and ascertain whether those prostheses will provide the desired leg length, offset, range of mobility, and other surgical goals, all without actually performing a trial reduction. For example, the surgeon may select a particular combination of prosthetic acetabulum and femoral components and "try" these by instructing the controller 22 to assemble these to the patient using the pelvic and femoral coordinate systems and hip center of rotation determined as described above, as well as data input by the surgeon or otherwise and defining the desired leg length, offset, and other parameters. The controller 22 retrieves the requisite dimensions of these components from its database, "assembles" these components virtually as they would ultimately be assembled physically, and tests the range of motion of the selected components in order to determine the characteristics of the resultant combination. The results (e.g., computed leg length, offset, range of motion, etc.) preferably are provided on visual display 30, but may also be provided in other form, e.g., as a hardcopy printout, etc Dependent on the results, the surgeon may proceed to implant the selected components, or may select one or more alternative components for virtual testing until the best available fit is found. The system thus guides the surgeon to the best available fit without unnecessary physical assembly/disassembly of components before the final assembly.

What is claimed is:

1. A method for providing, without using a patient tracker, a patient-specific pelvic coordinate system from a single near AP intra-operative image of the patient, said method comprising:

forming a single intra-operative fluoroscopic image of the patient's pelvis in the near AP direction using an x-ray source;

defining first and second landmarks on anatomically separated regions of said pelvis on said image, said landmarks being separated from each other in at least an anterior-posterior direction;

determining the transaxial displacement of said landmarks on said image;

determining the axial displacement of said landmarks on said image;

calculating by a processor the axial rotation of the pelvis using the transaxial displacement as a measure of the axial rotation of said pelvis with respect to the plane of said image, and calculating by a processor the transaxial rotation of the pelvis using said axial displacement as a measure of the transaxial rotation of said pelvis with the respect to the plane of said image.

2. The method of claim 1 in which the axial rotation of the pelvis is calculated as a function of the transaxial displacement and the distance between the x-ray source and the image plane.

3. The method according to claim 1 wherein said first landmark comprises the image point of the public symphysis.

4. The method according to claim 1 wherein the second landmark comprises the midpoint of a line between corresponding points on said image of the left and right sacroiliac joints.

5. The method according to claim 1 wherein said displacements are normalized with respect to the separation between a further pair of landmarks on the pelvis.

6. The method according to claim 5 wherein said further pair of landmarks comprises the left and right teardrops.

\* \* \* \* \*

UNITED STATES PATENT AND TRADEMARK OFFICE
CERTIFICATE OF CORRECTION

| | | |
|---|---|---|
| PATENT NO. | : 8,078,254 B2 | |
| APPLICATION NO. | : 10/565921 | |
| DATED | : December 13, 2011 | |
| INVENTOR(S) | : Stephen B. Murphy | |

It is certified that error appears in the above-identified patent and that said Letters Patent is hereby corrected as shown below:

IN THE SPECIFICATIONS:

Col. 4, line 38: "cally, crosses the adductionl/abduction axis, determined"

should read:

"cally, crosses the adduction/abduction axis, determined".

Signed and Sealed this
Fourteenth Day of February, 2012

David J. Kappos
*Director of the United States Patent and Trademark Office*